United States Patent
Favero et al.

(10) Patent No.: US 10,968,171 B2
(45) Date of Patent: *Apr. 6, 2021

(54) FRACTURING FLUID COMPRISING A (CO)POLYMER OF A HYDRATED CRYSTALLINE FORM OF 2-ACRYLAMIDO-2-METHYLPROPANE SULPHONIC ACID AND HYDRAULIC FRACTURING METHOD

(71) Applicant: S.P.C.M. SA, Andezieux Boutheon (FR)

(72) Inventors: Cédrick Favero, Andezieux Boutheon (FR); Johann Kieffer, Andezieux Boutheon (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/494,605

(22) PCT Filed: Mar. 19, 2018

(86) PCT No.: PCT/FR2018/050661
§ 371 (c)(1),
(2) Date: Sep. 16, 2019

(87) PCT Pub. No.: WO2018/172684
PCT Pub. Date: Sep. 27, 2018

(65) Prior Publication Data
US 2020/0048535 A1 Feb. 13, 2020

(30) Foreign Application Priority Data
Mar. 20, 2017 (FR) ...................................... 1752288

(51) Int. Cl.
*E21B 43/26* (2006.01)
*C07C 309/15* (2006.01)
(Continued)

(52) U.S. Cl.
CPC .............. *C07C 309/15* (2013.01); *C02F 1/56* (2013.01); *C02F 11/147* (2019.01); *C08F 20/58* (2013.01);
(Continued)

(58) Field of Classification Search
CPC ...... C07C 309/15; C02F 1/56; C02F 2103/10; C08F 1/56; C09K 8/588; C09K 8/68;
(Continued)

(56) References Cited

U.S. PATENT DOCUMENTS 3,727,689 A 4/1973 Clampitt
3,734,873 A * 5/1973 Anderson et al. .... C02F 1/5227
523/336
(Continued)

FOREIGN PATENT DOCUMENTS

GB 951147 3/1964

OTHER PUBLICATIONS

International Search Report (and English translation) and Written Opinion of the International Searching Authority for International Application No. PCT/FR2018/050661 dated Jun. 1, 2018.
(Continued)

*Primary Examiner* — Silvana C Runyan
(74) *Attorney, Agent, or Firm* — Heslin Rothenberg Farley & Mesiti P.C.

(57) ABSTRACT

The present invention relates to a fracturation fluid comprising at least one propping agent and at least one water-soluble (co)polymer prepared from the hydrated crystalline form of 2-acrylamido-2-methylpropane sulfonic acid and/or at least one of its salts. The invention relates to a process to prepare said fluid, and to a hydraulic fracturation process using said fluid.

20 Claims, 2 Drawing Sheets

Figure 1:
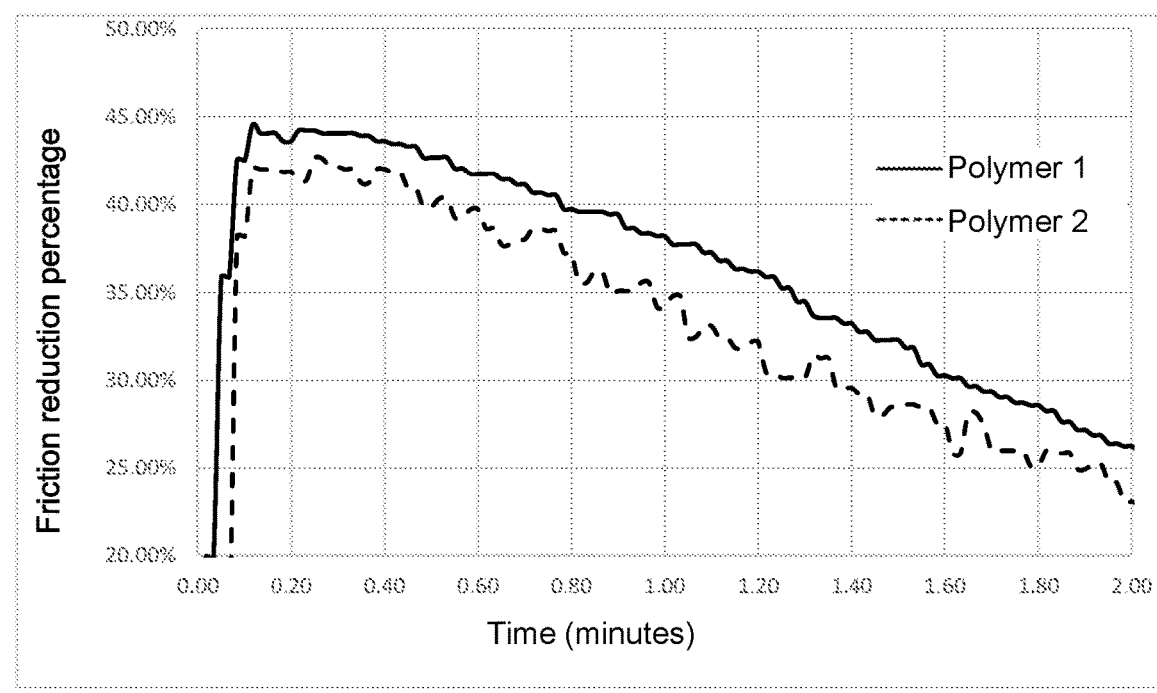

(51) Int. Cl.
*C08F 20/58* (2006.01)
*C09K 8/68* (2006.01)
*C09K 8/80* (2006.01)
*C09K 8/588* (2006.01)
*E21B 43/16* (2006.01)
*C02F 11/147* (2019.01)
*C02F 1/56* (2006.01)
*C02F 103/10* (2006.01)

(52) U.S. Cl.
CPC ............... *C09K 8/588* (2013.01); *C09K 8/68* (2013.01); *C09K 8/80* (2013.01); *E21B 43/16* (2013.01); *E21B 43/26* (2013.01); *C02F 2103/10* (2013.01); *C07B 2200/13* (2013.01); *C09K 2208/28* (2013.01)

(58) Field of Classification Search
CPC ....... C09K 8/80; C09K 2208/28; E21B 43/16; E21B 43/26; C07B 2200/13
See application file for complete search history.

(56) References Cited

U.S. PATENT DOCUMENTS

| | | |
|---|---|---|
| 3,841,402 A | 10/1974 | Knight et al. |
| 3,888,312 A | 6/1975 | Tiner et al. |
| 3,938,594 A | 2/1976 | Rhudy et al. |
| 4,033,415 A | 7/1977 | Holtmyer et al. |
| 4,801,389 A | 1/1989 | Brannon et al. |
| 10,759,746 B2 | 9/2020 | Favero et al. |
| 2009/0260819 A1* | 10/2009 | Kurian .................. C09K 8/588 166/292 |
| 2009/0298721 A1* | 12/2009 | Robb ...................... C09K 8/68 507/209 |
| 2010/0122816 A1* | 5/2010 | Lewis ................. C04B 40/0039 166/280.2 |
| 2010/0274048 A1 | 10/2010 | Wakayama |
| 2013/0255954 A1 | 10/2013 | Favero et al. |
| 2020/0079992 A1 | 3/2020 | Favero et al. |
| 2020/0087186 A1 | 3/2020 | Favero et al. |

OTHER PUBLICATIONS

Favero et al., "Hydrated Crystalline Form of 2-Acrylamido-2-Methylpropane Sulfonic Acid," U.S. Appl. No. 16/926,159, filed Jul. 10, 2020, 58 pp.

\* cited by examiner

FRACTURING FLUID COMPRISING A (CO)POLYMER OF A HYDRATED CRYSTALLINE FORM OF 2-ACRYLAMIDO-2-METHYLPROPANE SULPHONIC ACID AND HYDRAULIC FRACTURING METHOD

CROSS REFERENCE TO RELATED APPLICATIONS

This application is a national stage filing under section 371 of International Application No. PCT/FR2018/050661 filed on Mar. 19, 2018, and published on Sep. 27, 2018 as WO 2018/172684, which claims priority to French Application No. 1752288, filed on Mar. 20, 2017. The entire contents of WO 2018/172684 are hereby incorporated herein by reference.

FIELD OF THE INVENTION

The invention relates to a new fracturation fluid comprising at least one propping agent and at least one water-soluble (co)polymer prepared from the hydrated crystalline form of 2-acrylamido-2-methylpropane sulfonic acid and/or at least one of its salts.

The invention also relates to a hydraulic fracturation method for unconventional underground oil and gas reservoirs using said composition.

PRIOR ART

The production of oil (hydrocarbons) and gas contained in unconventional underground reservoirs has been developed for several years and requires fractures to be opened in the reservoir for economical oil and gas production.

In the rest of the description of the prior art and of the invention, "unconventional underground reservoirs" means deposits requiring specific extraction technologies because they do not exist in the form of an accumulation in porous and permeable rock (see *Les hydrocarbures de roche-mère en France Rapport provisoire—CGIET No.* 2011-04-G—*Ministry of Ecology, Sustainable Development, Transport and Housing—April* 2011). For unconventional gas, mention may be made of shale gas, coal bed methane, and tight gas. For unconventional oil, mention may be made of heavy oil, shale oil, and tight oil.

The reserves contained in the unconventional reservoirs are enormous and extremely widely spread in areas that were formerly unexploitable like bedrock hydrocarbons such as clay shale, tight gas, and coal bed methane. In the United States, shale gas is widely exploited and now represents 46% of total natural gas produced in the USA, whereas it only represented 28% in 1998. The widespread basins are known under the names of Barnett Shale, Ville Fayette Shale, Mowry Shale, Marcellus Shale, Utica Shale, etc. The exploitation of tight reservoirs was made possible by evolution of drilling techniques.

The production techniques have evolved from vertical wells to horizontal wells, reducing the number of production wells necessary and their footprint on the ground and better covering the volume of the reservoir to recover the maximum gas or oil. However, the permeabilities are insufficient for the hydrocarbon to migrate from the bedrock to the well easily, and thereby allow economically viable production of significant quantities of gas or oil. It is therefore necessary to increase the production permeability and surfaces by stimulation operations and particularly by hydraulic fracturation of the rock in contact with the well.

Hydraulic Fracturation

The goal of hydraulic fracturation is to create extra permeability and to cause higher gas and oil production surfaces. Indeed, low permeability, the natural barriers in tight layers, and impermeabilization by drilling operations greatly limit production. The gas or oil contained in the unconventional reservoir cannot easily migrate from the rock to the well without stimulation.

These hydraulic fracturation operations on horizontal wells began in 1960 in the Appalachians and, today, several tens of thousands of operations have taken place in the United States.

Technologies for studying, modeling the reservoir, drilling, cementing and stimulating have become more and more sophisticated and use equipment that can conduct these operations in shorter and shorter periods with precise analysis of results.

Reservoir Stimulation by Hydraulic Fracturation

These operations consist in injecting water at high pressure and very high flow rate so as to create fractures spread perpendicularly in production wells. Generally the process has several steps to create fractures along the length of the horizontal well, which allows the maximum volume of the reservoir to be covered.

To keep these fractures open, a propping agent is added (for example sand, plastic materials or calibrated ceramics) so as to prevent these fractures from closing and to maintain the capillarity created once injection ends.

Water alone does not suffice for obtaining effective propping agent placement because it has low viscosity. This limits its capacity to hold the propping agent in place in the fractures. To solve this problem, fracturation fluids have been developed, which contain viscosifying compound or compounds.

By definition, a compound is viscosifying when it increases the viscosity of solutions in which it is dissolved.

As well as having viscosifying properties, the compound must have a specific rheological profile. The compound must be able to generate a low viscosity so as not to hamper transport and pumping of the fluid containing the propping agent during the high shears undergone while the fracturation fluid is injected. Once injected, this same compound must be able to cause sufficient viscosity when the shear reduces to support the propping agent to hold it in the fractures.

The polymer must therefore provide rheofluidifying properties to the solution to have relatively low viscosity when injected (at high shear) and high viscosity to hold the propping agent in suspension in the fracture when the shear decreases.

The viscoelastic properties of the polymers in solution must also be taken into consideration. This viscoelasticity, and its importance in the application, is described in document SPE 147206 (Fracturing Fluid Comprised of Components Sourced Solely from the Food Industry Provides Superior Proppant Transport—David Loveless, Jeremy Holtsclaw, Rajesh Saini, Phil Harris, and Jeff Fleming, SPE, Halliburton) through visual observations in static or dynamic experiments, or by rheology measurements, such as the measurement of viscous and elastic moduli (G' and G"), or the measurement of viscosity as a function of shear on rheometers. Accordingly, elastic properties will be advantageous to ensure the transport and suspension of the propping agent of the fracture.

The choice of polymer is therefore not obvious and requires deep rheological study to produce satisfactory results.

Among viscosifying compounds for aqueous solutions belonging to the state of the art, mention may be made of natural substances such as guar gums and their derivatives such as hydroxypropylguar (HPG) or carboxymethylhydroxypropyl guar (CMHPG); cellulose derivatives such as carboxymethyl cellulose or hydroxyethyl cellulose. These compounds are described in particular in U.S. Pat. Nos. 4,033,415, 3,888,312 and 4,801,389. In document SPE 152596 (Hydraulic Fracturing 101: What Every Representative, Environmentalist, Regulator, Reporter, Investor, University Researcher, Neighbor and Engineer Should Know About Estimating Frac Risk and Improving Frac Performance in Unconventional Gas and Oil Wells—George E. King, Apache Corporation), the latest advances on the performance of fracturation fluids are discussed in detail.

However, these natural substances, and particularly guar gum derivatives, are also useful in other applications, like the food or textile industry, and the development of exploitation of unconventional oil and gas resources competes with these other applications. This creates availability pressure on these products and causes pricing problems.

Other petrochemical compounds may have viscosifying properties. Mention may be made of synthetic polymers. Poly(meth)acrylamides, optionally partially hydrolyzed, and poly(meth)acrylates and their copolymers are particularly known. These polymers develop viscosifying due to their molar mass and interchain ionic repulsions. These polymers are described in patents GB951147, U.S. Pat. No. 3,727,689, 3,841,402 or 3,938,594. The mechanism governing viscosity is related to increasing hydrodynamic volume due to intrachain repulsions, interchain tangling, etc.

However, in the presence of high salinity or a high temperature of use, these polymers do not develop high tangling and repulsions, which translates to a substantial reduction in viscosifying power especially after having undergone the shear in the pumping step. Moreover, these polymers do not generally present sufficient viscoelastic properties to support the propping agent in the fracture. The proportion of these polymers must be raised to levels that are too high to produce the propping agent's suspension properties. The proportions are not economically viable.

The polymers used to have the viscosifying properties may advantageously also be friction reducers that reduce the loss of charge in turbulent mediums and greatly increase the flow rate at identical power and pipe diameter.

Synthetic polymers containing 2-acrylamido-2-methylpropane sulfonic acid and/or its salts present interesting friction reduction properties in aqueous solution. These polymers are also known for their shear resistance and thermal degradation, in particular in saline solutions. However, producing very high molecular weight polymer containing 2-acrylamido-2-methylpropane sulfonic acid is difficult without allowing for polymers having solubility problems when their molecular weight increases. So, to have optimal friction reduction phenomenon and high viscosity generation, it is essential that the polymer dissolves quickly, particularly in saline solution, and that it has a very high molecular weight.

DESCRIPTION OF THE INVENTION

The Applicant has found and developed a fracturation fluid that has a very high friction reduction effect while guaranteeing an improved viscosifying effect in saline solution (brine) or non-saline solution (water).

What is more, the good polymer solubility of the fracturation fluid combined with its sulfonated anionic character prevents it from being adsorbed in the rock, which causes regained conductivity and therefore increased oil (hydrocarbons) and gas production yield. The oil (or oils) from an underground formation is also called petroleum. This is generally a mixture of hydrocarbons.

A first feature of the invention relates to the use of a fracturation fluid comprising at least one propping agent and at least one water-soluble (co)polymer made from the hydrated crystalline form of 2-acrylamido-2-methylpropane sulfonic acid and/or at least one of its salts.

A second feature of the invention relates to a manufacturing process for the production of a fracturation fluid with at least one water-soluble (co)polymer prepared from the hydrated crystalline form of 2-acrylamido-2-methylpropane sulfonic acid and/or at least one of its salts.

A third feature of the invention relates to a hydraulic fracturation process for an unconventional underground oil or gas reservoir using the fracturation fluid according to the invention.

A fourth feature of the invention relates to a friction reduction process using a fracturation fluid in a hydraulic fracturation operation for an unconventional underground oil or gas reservoir using the fracturation fluid according to the invention.

By definition, a water-soluble (co)polymer is a (co)polymer that gives an aqueous solution without insoluble particles when it is dissolved with stirring at 25° C. and with a concentration of 50 g·L$^{-1}$ in water.

The propping agent can be chosen in a non-restrictive manner from sand, ceramics, bauxite, glass beads, and sand impregnated with resin. It represents preferably from 0.5 to 40%, more preferably from 1 to 25% and even more preferably from 1.5 to 20%, by weight of the fracturation fluid.

The fracturation fluid according to the invention is preferably obtained from between 0.001% and 1% by weight of water-soluble (co)polymer according to the invention, preferably between 0.002% and 0.2%, by weight of the fracturation fluid.

The fracturation fluid may comprise other compounds known to the person of skill in the art, like those cited in document SPE 152596, for example:

Anti-swelling agents for clays like potassium chloride or choline chloride, and/or Biocides to prevent the development of bacteria, particularly sulfate-reducing bacteria that can form viscous masses reducing the passage surface areas. Mention may for example be made of glutaraldehyde, which is the most used, or formaldehyde or isothiazolinones, and/or Oxygen reducers like ammonium bisulfate to prevent the destruction of other components by oxidation and corrosion of injection tubes, and/or Anticorrosion additives to protect the tubes from oxidation by the residual oxygen, N,N-dimethylformamide being preferred, and/or Lubricants like oil distillates, and/or Iron chelators like citric acid, EDTA (ethylene diamine tetra-acetic acid), phosphonates, and/or Antitartar products like phosphates, phosphonates, polyacrylates or ethylene glycol.

The hydrated crystalline form of 2-acrylamido-2-methylpropane sulfonic acid has a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees. The uncertainty in these peaks is generally of the order of 0.1°.

X-ray crystallography, radiocrystallography or X-ray diffractometry is an analytical technique for studying the structure of the crystalline material on the atomic scale. It uses the physical phenomenon of X-ray diffraction. A diffractometer having a copper source may be used.

A powder formed from a specific crystalline phase will always produce diffraction peaks in the same directions. So this diffraction diagram forms a real signature of the crystalline phase. It is therefore possible to determine the nature of each crystalline phase within a mixture or a pure product.

This signature is specific to each crystalline organic or inorganic compound, and presents in the form of a list of peaks with positions at the 2θ angle (2-theta).

This technique is used to characterize the material, particularly the different crystalline forms that may exist for a given chemical molecule.

The hydrated crystalline form of 2-acrylamido-2-methylpropane sulfonic acid has a Fourier transform infrared spectrum comprising peaks at 3280 $cm^{-1}$, 3126 $cm^{-1}$, 1657 $cm^{-1}$, 1595 $cm^{-1}$, 1453 $cm^{-1}$, 1395 $cm^{-1}$, 1307 $cm^{-1}$, 1205 $cm^{-1}$, 1164 $cm^{-1}$, 1113 $cm^{-1}$, 1041 $cm^{-1}$, 968 $cm^{-1}$, 885 $cm^{-1}$, 815 $cm^{-1}$, 794 $cm^{-1}$. The uncertainty in these peaks is generally of the order of 8 $cm^{-1}$. Advantageously, this is the solid spectrum obtained conventionally in a salt such as KBr.

Fourier transform infrared spectroscopy is the analysis of vibrations emitted, absorbed or diffused by the molecules. This technique is sensitive to close interactions (influence of the lattice unit on the bonds). In the majority of cases, the Fourier transform infrared spectra for different crystalline systems differ significantly. So the Fourier transform infrared spectrum reflects details about the crystalline structure of an organic compound.

Generally, and unless otherwise indicated, the X-ray diffraction diagram and the infrared spectrum are obtained at 20° C. and atmospheric pressure of 1 atmosphere (101,325 Pa).

The hydrated crystalline form of 2-acrylamido-2-methylpropane sulfonic acid has minimum ignition energy greater than 400 mJ, preferably greater than 500 mJ (1 $mJ=10^{-3}$ Joule).

The minimum ignition energy represents the minimum energy that must be provided to a compound to cause ignition. The energy may be electric or thermal. The minimum ignition energy is an essential piece of data for taking into account the risk of explosion during product handling (transfer, storage, reaction, shaping, etc.).

The minimum ignition energy depends on the powder's properties (composition) and its macromolecular structure (particle size, crystalline form, specific surface area).

For solids, this energy is the minimum energy of an electrical spark that can ignite a cloud of dust. The higher the minimum ignition energy, the lower the risk the solid presents during use, handling, storage.

Minimum ignition energy was measured according to standard NF EN 13821.

The hydrated crystalline form of 2-acrylamido-2-methylpropane sulfonic acid presents 4 thermal phenomena with the differential scanning calorimetry technique, at 70° C., 100° C., 150° C. and 190° C. The relative uncertainty when observing these phenomena is generally of the order of 10° C., advantageously 5° C. or less.

The thermal phenomena are measured by differential scanning calorimetry (DSC). This technique measures the heat variation associated with thermal denaturation of the compound when it is heated at a constant rate, for example with a heating ramp of 10° C./minute.

It is generally recognized that the thermal phenomenon that occurs at 190° C. (+/−10° C.) is related to the melting point of 2-acrylamido-2-methylpropane sulfonic acid.

According to a specific embodiment of the invention, the water-soluble (co)polymer is obtained at least from 2-acrylamido-2-methylpropane sulfonic acid and/or from at least one of its salts, 50 mol % to 100 mol % of 2-acrylamido-2-methylpropane sulfonic acid being advantageously in the hydrated crystalline form and/or at least one of its salts, more advantageously 70 to 100 mol %, and even more advantageously 100 mol %.

The water-soluble (co)polymer is advantageously obtained from between 1 and 100 mol % of 2-acrylamido-2-methylpropane sulfonic acid, preferably between 2 and 60 mol % of 2-acrylamido-2-methylpropane sulfonic acid, even more preferably between 5 and 30 mol % of 2-acrylamido-2-methylpropane sulfonic acid; even more preferably between 5 and 15 mol % of 2-acrylamido-2-methylpropane sulfonic acid; 50 mol % to 100 mol % of 2-acrylamido-2-methylpropane sulfonic acid being advantageously in the hydrated crystalline form, and/or at least one of its salts, more advantageously 70 to 100 mol %, and even more advantageously 100 mol %.

Generally, the person skilled in the art will know how to adjust the quantity of any additional monomers (anionic and/or cationic and/or zwitterionic) listed below to reach 100 mol %.

Generally, unless otherwise indicated, "2-acrylamido-2-methylpropane sulfonic acid in hydrated crystalline form" denotes the acid form and/or the salified form. The same is the case for the anionic monomers that may denote the acid and/or salified forms like, for example, for acrylic acid.

According to a preferred embodiment of the invention, the (co)polymer of the invention is obtained from that saline form of 2-acrylamido-2-methylpropane sulfonic acid in hydrated crystalline form. 2-acrylamido-2-methylpropane sulfonic acid is therefore preferably partially or totally salified before polymerization. The acid form of a monomer can be salified before and/or during and/or after the (co) polymerization of the monomer or monomers.

The salt form is advantageously obtained from a compound chosen from among an alkali or alkaline earth metal hydroxide, an alkali or alkaline metal earth oxide, ammonia, an amine having the following formula $NR_1R_2R_3$ ($R_1$, $R_2$ and $R_3$ being advantageously hydrocarbon groups, in particular alkyl groups) or an alkali or alkaline earth metal carbonate. A preferred alkaline metal is sodium.

The water-soluble (co)polymer is preferably obtained from the hydrated crystalline form of 2-acrylamido-2-methylpropane sulfonic acid and/or from at least one of its salts, and from at least one nonionic monomer, and/or at least one anionic monomer, and/or at least one cationic monomer and/or at least one zwitterionic monomer.

The nonionic monomer or monomers that can be used in the scope of the invention can be chosen, in particular, in the group comprising water-soluble vinyl monomers. Preferred monomers belonging to this class are, for example, acrylamide, methacrylamide, N-isopropylacrylamide, N,N-dimethylacrylamide, N,N-diethylacrylamide and N-methylolacrylamide. The following may also be used: N-vinylformamide, N-vinyl acetamide, N-vinylpyridine and N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol. A preferred nonionic monomer is acrylamide.

According to a particular embodiment, the water-soluble (co)polymer is advantageously obtained from the hydrated crystalline form of 2-acrylamido-2-methylpropane sulfonic acid or of at least one of its salts and from between 1 and 99 mol % of nonionic monomer(s), preferably between 40 and 95 mol % and more preferably between 45 and 90 mol %, relative to the total number of monomers. In this case, the (co)polymer is advantageously obtained from between 1 and 99 mol % of 2-acrylamido-2-methylpropane sulfonic acid and/or at least one of its salts; and more preferably between 2 and 60 mol %; 50 mol % to 100 mol % of 2-acrylamido-2-methylpropane sulfonic acid being advantageously in the hydrated crystalline form and/or at least one of its salts, more advantageously 70 to 100 mol %, and even more advantageously 100 mol %.

The anionic monomer(s) that may be used within the scope of the invention may be selected from a wide group. These monomers may have acrylic, vinyl, maleic, fumaric, malonic, itaconic, allylic functional groups and contain a carboxylate, phosphonate, phosphate, sulfate, sulfonate group or another anionic group. The anionic monomer may be in acid form or in the form of an alkaline earth metal salt, an alkali metal salt or an ammonium salt. Examples of suitable monomers include acrylic acid, methacrylic acid, itaconic acid, crotonic acid, maleic acid, fumaric acid, acrylamido undecanoic acid, 3-acrylamido 3-methylbutanoic acid, maleic anhydride; monomers of the strong acid type having for example a function of the sulfonic acid or phosphonic acid type, such as vinylsulfonic acid, vinylphosphonic acid, allylsulfonic acid, methallylsulfonic acid, 2-methylidenepropane-1,3-disulfonic acid, 2-sulfoethyl-methacrylate, sulfopropylmethacrylate, sulfopropylacrylate, allylphosphonic acid, styrene sulfonic acid, 2-acrylamido-2-methyl propane disulfonic acid; and water-soluble salts of these monomers like their alkali metal, alkaline earth metal, or ammonium salts. In this list, the strong acid monomers mentioned having a sulfonic acid function do not include the hydrated crystalline form of 2-acrylamido-2-methylpropane sulfonic acid and/or of its salts.

According to a particular embodiment, the copolymer is advantageously obtained from between 1 and 99 mol % of anionic monomer(s), preferably between 2 and 60 mol % and more preferably between 3 and 50 mol %, relative to the total number of monomers. In this case, these percentages also include the hydrated crystalline form of 2-acrylamido-2-methylpropane sulfonic acid and/or its salts.

The cationic monomer or monomers that can be used in the scope of the invention may be chosen from among monomers derived from units of the acrylamide, acrylic, vinyl, allyl or maleic type, where these monomers have a quaternary phosphonium or ammonium function. Mention may be made, in particular and in a non-limiting way, of quaternized dimethylaminoethyl acrylate, quaternized dimethylaminoethyl acrylate, dimethyldiallylammonium chloride (DADMAC), acrylamido propyltrimethyl ammonium chloride (APTAC) and methacrylamido propyltrimethyl ammonium chloride (MAPTAC). The quaternization agent may be chosen from alkyl chlorides, dialkyl sulfates or alkyl halides. Preferably, the quaternization agent is chosen from methyl chloride or diethyl sulfate.

The acidified salts are obtained by means known to a person skilled in the art, and notably by protonation. The quaternized salts are also obtained by means known to a person skilled in the art notably, by reaction with benzyl chloride, methyl chloride (MeCl), aryl, alkyl chlorides, or dialkylsulfates such as dimethylsulfate.

According to a preferred embodiment, the cationic monomer is selected from the diallyldialkyl ammonium salts such as diallyl dimethyl ammonium chloride (DADMAC), the acidified or quaternized salts of dialkyl-aminoalkylacrylamides or methacrylamides, such as for example methacrylamido-propyl trimethyl ammonium chloride (MAPTAC), acrylamido-propyl trimethyl ammonium chloride (APTAC).

The zwitterionic monomer may be a derivative of a unit of the acrylamide, acrylic, vinyl, allyl or maleic type, this monomer having an amine or quaternary ammonium function and an acid function of the carboxylic (or carboxylate), sulfonic (or sulfonate) or phosphoric (or phosphate) type. Mention may be made, specifically and in a non-limiting manner, of dimethylaminoethyl acrylate derivatives, such as 2-((2-(acryloyloxy)ethyl) dimethylammonio) ethane-1-sulfonate, 3-((2-(acryloyloxy)ethyl) dimethylammonio) propane-1-sulfonate, 4-((2-(acryloyloxy)ethyl) dimethylammonio) butane-1-sulfonate, [2-(acryloyloxy)ethyl] (dimethylammonio) acetate, dimethylaminoethyl methacrylate derivatives such as 2-((2-(methacryloyloxy) ethyl) dimethylammonio) ethane-1-sulfonate, 3-((2-(methacryloyloxy) ethyl) dimethylammonio) propane-1-sulfonate, 4-((2-(methacryloyloxy) ethyl) dimethylammonio) butane-1-sulfonate, [2-(methacryloyloxy)ethyl] (dimethylammonio) acetate, dimethylamino propylacrylamide derivatives such as 2-((3-acrylamidopropyl) dimethylammonio) ethane-1-sulfonate, 3-((3-acrylamidopropyl) dimethylammonio) propane-1-sulfonate, 4-((3-acrylamidopropyl) dimethylammonio) butane-1-sulfonate, [3-(acryloyloxy) propyl)] (dimethylammonio) acetate, dimethylamino propyl methylacrylamide derivatives such as 2-((3-methacrylamidopropyl) dimethylammonio) ethane-1-sulfonate, 3-((3-methacrylamidopropyl) dimethylammonio) propane-1-sulfonate, 4-((3-methacrylamidopropyl) dimethylammonio) butane-1-sulfonate and [3-(methacryloyloxy)propyl] (dimethylammonio) acetate.

Monomers with a hydrophobic nature may also be used in the preparation of the water-soluble (co)polymer used in the method of the invention. They are preferably selected from the group consisting of (meth)acrylic acid esters having an alkyl, arylalkyl, propoxylated or ethoxylated chain, (meth)acrylamide derivatives with an alkyl, arylalkyl or dialkyl propoxylated, ethoxylated, or ethoxylated and propoxylated chain; (meth)acrylamide derivatives having an alkyl, arylalkyl, propoxylated, ethoxylated, ethoxylated and propoxylated, or dialkyl chain; alkyl aryl sulfonates.

When a monomer having a hydrophobic nature is used for the preparation of the water-soluble (co)polymer, its quantity lies advantageously within the range inclusively between 0.001 and 3 mol % relative to the total quantity of monomers.

Monomers with a fluorescent function may also be used in the scope of the invention. A monomer with a fluorescent function may be detected by any appropriate method, for example by fluorimetry with a fixed wavelength fluorimeter. Generally, the monomer having a fluorescent function is detected at the excitation and emission maxima, which can be determined using a scanning fluorimeter.

Monomers having a fluorescent function are chosen from, for example, monomers of the sodium sulfonate styrene or sulfonic styrene type.

The water-soluble (co)polymer is preferably an anionic (co)polymer containing acrylamide and 2-acrylamido-2-methylpropane sulfonic acid; 50 mol % to 100 mol % of 2-acrylamido-2-methylpropane sulfonic acid being in the hydrated crystalline form and/or at least one of its salts. Preferably, it is a terpolymer of acrylamide, acrylic acid and 2-acrylamido-2-methylpropane sulfonic acid; 50 mol % to 100 mol % of 2-acrylamido-2-methylpropane sulfonic acid being in the hydrated crystalline form and/or at least one of its salts. In both cases, the (co)polymer may be partially or totally post hydrolyzed.

The water-soluble (co)polymer is preferably obtained from between 1 mol % and 99 mol % of anionic monomer (s), more preferably between 2 mol % and 60 mol %, where these percentages include the monomer corresponding to the hydrated crystalline form of 2-acrylamido-2-methylpropane sulfonic acid or one of its salts.

In a preferred manner, the water-soluble (co)polymer according to the invention is anionic or amphoteric and is obtained from between 1 and 99 mol % of anionic monomers, these percentages including the monomer corresponding to the hydrated crystalline form of 2-acrylamido-2-methylpropane sulfonic acid or one of its salts. The water-soluble (co)polymer according to the invention is preferably a copolymer of a salt of the hydrated crystalline form of 2-acrylamido-2-methylpropane sulfonic acid and acrylamide.

The water-soluble (co)polymer according to the invention is preferably an anionic polymer obtained by copolymerization of a salt in the hydrated crystalline form of 2-acrylamido-2-methylpropane sulfonic acid with an acrylic acid salt, or an anionic polymer obtained by copolymerization of a salt of 2-acrylamido-2-methylpropane sulfonic acid in hydrated crystalline form with a nonionic hydrolyzable monomer.

The nonionic hydrolyzable monomer is preferably chosen from acrylamide, methacrylamide, N-mono derivatives of acrylamide or methacrylamide, N,N derivatives of acrylamide or methacrylamide, and acrylic or methacrylic esters. The preferred nonionic monomer is acrylamide.

According to the invention, the water-soluble (co)polymer used may have a linear, branched, star-shaped, comb-shaped or block structure. These structures may be obtained by the selection of the initiator, transfer agent, polymerization technique, such as controlled radical polymerization known as RAFT (reversible-addition fragmentation chain transfer), NMP (nitroxide-mediated polymerization) or ATRP (atom-transfer radical polymerization), incorporation of structural monomers, or concentration, etc.

According to the invention, the water-soluble (co)polymer is advantageously linear or structured. Structured (co) polymer denotes a non-linear (co)polymer that has side chains so as to obtain, when this (co)polymer is dissolved in water, a high state of tangling leading to viscosities with very high low gradients. The water-soluble (co)polymer according to the invention is not generally crosslinked.

The water-soluble (co)polymer may in addition be structured:
- by at least one structure agent, which can be chosen from the group comprising unsaturated polyethylene monomers (having at least two unsaturated functions), such as for example vinyl, allyl, acrylic and epoxy functions, and for example mention may be made of methylene-bis-acrylamide (MBA), triallyamine, tetraallylammonium chloride, or 1,2-dihydroxyethylene bis-(N-acrylamide), and/or
- by macroinitiators such as polyperoxides, polyazoics and poly transfer agents such as polymercaptan (co)polymers, and polyols, and/or
- by functionalized polysaccharides.

The quantity of branching/crosslinking agent in the monomer mixture is advantageously less than 4% by weight relative to the monomer content, more advantageously less than 1% and even more advantageously less than 0.5%. According to a specific embodiment, it may at least be equal to 0.00001% by weight relative to the monomer content.

Generally, the (co)polymer does not require the development of any particular polymerization method. Indeed, it may be obtained according to polymerization techniques known by a person skilled in the art. It may notably be solution polymerization, gel polymerization, precipitation polymerization, emulsion polymerization (aqueous or inverse), suspension polymerization, reactive extrusion polymerization, or micellar polymerization.

Polymerization is generally a free-radical polymerization preferably by inverse emulsion polymerization or gel polymerization. By free-radical polymerization, we include free-radical polymerization by means of UV initiators, azo initiators, redox or thermal initiators as well as controlled radical polymerization (CRP) or matrix polymerization techniques.

According to a specific embodiment of the invention, the (co)polymer may be post-hydrolyzed. Post-hydrolysis is the reaction of the (co)polymer after polymerization. This step consists in reacting the hydrolyzable functional groups on the advantageously nonionic monomers, more advantageously amide or ester functions, with a hydrolysis agent. This hydrolysis agent may be an enzyme, an ion exchange resin, or an alkali metal. Preferably, the hydrolysis agent is a base. During this (co)polymer post-hydrolysis step, the number of carboxylic acid functions increases. The reaction between the base and the amide or ester functions in the (co)polymer produces carboxylate groups.

According to the invention, the (co)polymer may be in the form of a liquid, gel or solid when its preparation includes a drying step such as spray drying, tumble drying, drying by electromagnetic radiation such as microwave or fluidized bed drying.

According to a specific embodiment, the water-soluble (co)polymer may comprise at least one LCST group.

According to the general knowledge of a person skilled in the art, LCST groups correspond to groups whose water solubility for a determined concentration is modified beyond a certain temperature and as a function of the salinity. This is a group having a heating transition temperature defining its lack of affinity with the solvent medium. The lack of affinity with the solvent results in opacification or loss of transparency, which may be due to precipitation, aggregation, gelification, or viscosification of the medium. The minimum transition temperature is known as "LCST" (Lower Critical Solution Temperature). For each concentration of the LCST group, a heating transition temperature is observed. It is greater than the LCST, which is the minimum point in the curve. Below this temperature, the polymer is soluble in water; above this temperature, the polymer loses its solubility in water.

According to a specific embodiment, the water-soluble (co)polymer may comprise at least one UCST group.

According to the general knowledge of a person skilled in the art, UCST groups correspond to groups whose water solubility for a determined concentration is modified beyond a certain temperature and as function of the salinity. This is a group having a cooling transition temperature defining its lack of affinity with the solvent medium. The lack of affinity with the solvent results in opacification or loss of transparency, which may be due to precipitation, aggregation, gelification, or viscosification of the medium. The maximum transition temperature is known as "UCST" (Upper Critical Solution Temperature). For each concentration of the UCST group, a cooling transition temperature is observed. It is lower than the UCST, which is the maximum point in the curve. Above this temperature, the (co)polymer is soluble in water; below this temperature, the (co)polymer loses its water solubility.

According to the invention, the water-soluble (co)polymer has an advantageously high molecular weight. "High molecular weight" denotes molecular weights of at least 0.5 million g/mol, preferably between 10 and 40 million g/mol, more preferably between 15 and 30 million g/mol. Molecular weight is understood as average molecular weight by weight. It is measured by measuring intrinsic viscosity (Mark-Houwink formula).

Before it is used in the fracturation fluid, the water-soluble (co)polymer according to the invention may be found in different solid or liquid forms. Preferably, it is found in the form of a powder, an inverse water-in-oil emulsion, or in an aqueous or oil particulate polyphasic suspension.

A second feature of the invention relates to a preparation process for a fracturation fluid with at least one water-soluble (co)polymer prepared from the hydrated crystalline form of 2-acrylamido-2-methylpropane sulfonic acid and/or at least one of its salts, in which the (co)polymer is used in water or brine, and in which the water-soluble (co)polymer is, before formation of the fracturation fluid:
Either in powder form;
Or in the form of a water-in-oil inverse emulsion;
Or in the form of an aqueous or oil particulate polyphasic suspension.

The preparation process for a fracturation fluid according to the invention preferably comprises a step of adding into the fluid at least one propping agent as described previously.

When the water-soluble (co)polymer used in the fracturation fluid is, before formation of the fracturation fluid, in powder form, the particle size is preferably less than 1.5 millimeters, more preferably less than 850 micrometers, even more preferably less than 200 micrometers.

The particle size refers to the average diameter measured with a laser diffraction particle analyzer according to the conventional techniques of the person skilled in the art. An example of the device to measure the average diameter is the Mastersizer by Malvern Instruments.

When the water-soluble (co)polymer used in the fracturation fluid is, before formation of the fracturation fluid, in the form of an inverse water-in-oil emulsion, the (co)polymer concentration in the emulsion is preferably inclusively between 5 and 60% by weight, more preferably between 15 and 40% by weight relative to the weight of the emulsion. In a preferred manner, the inverse water-in-oil emulsion contains by weight from 0.01% to 70% of an organic and/or inorganic salt, preferably between 5 and 20% by weight relative to the weight of the emulsion. The salts may be chosen in a non-restrictive manner from among sodium chloride, sodium sulfate, sodium bromide, ammonium sulfate, ammonium chloride, lithium chloride, lithium bromide, potassium chloride, potassium bromide, magnesium sulfate, aluminum sulfate and mixtures thereof. The preferred salts are ammonium chloride and ammonium sulfate.

When the water-soluble (co)polymer used in the fracturation fluid is, before formation of the fracturation fluid, in the form of an aqueous particulate polyphasic suspension, the (co)polymer is preferably in the form of a suspension.

In this case, the water-soluble (co)polymer used in the fracturation fluid is, before formation of the fracturation fluid, in the form of an aqueous particulate polyphasic suspension, comprising:
i. 15 to 60% by weight of at least one water-soluble (co)polymer according to the invention in the form of solid particles with average size inclusively between 5 and 500 µm;
ii. 15 to 45% by weight of at least one alkali metal salt and/or of at least one alkaline earth metal salt;
iii. at least one viscosifying agent other than the water-soluble (co)polymer according to the invention;
iv. at least 10% by weight of water; and
said suspension having Brookfield viscosity inclusively between 500 and 20,000 cps at a temperature of 20° C., and
said suspension having a density inclusively between 1.1 and 2 kg·L$^{-1}$.

When the water-soluble (co)polymer used in the fracturation fluid is in the form of a specific oily multi-phase suspension, said suspension comprises preferably:
i 15 to 60% by weight of at least one water-soluble (co)polymer according to the invention in the form of solid particles with average size inclusively between 5 and 500 µm;
ii at least one viscosifying agent other than the water-soluble (co)polymer according to the invention;
iii at least 10% by weight of oil; and
said suspension having a Brookfield viscosity inclusively between 500 and 20,000 cps at a temperature of 20° C., and
said suspension having a density inclusively between 0.6 and 1.4 kg·L$^{-1}$.

The Brookfield viscosity is measured with a Brookfield device, mounted with an LV spindle, where the spindle can turn at a rate of 30 rpm for example, where the measurement is advantageously conducted at 20° C. The density is measured at 20° C., at a pressure of 1 atm, i.e., 101,325 Pa.

A third feature of the invention relates to a hydraulic fracturation process for an unconventional underground oil or gas reservoir comprising the preparation of a fracturation fluid as described previously, and the injection of said fracturation fluid in an underground formation.

The injection is made under pressure so as to create fractures distributed along the production well.

Optionally, before, during or after the creation of fractures, at least one oxidizing compound and/or at least one surfactant compound is injected into the reservoir.

The surfactant injection removes the viscosity caused by the (co)polymer by inhibiting the hydrophobic interchain interactions, while the injection of the oxidizing compound destroys the (co)polymer. In both cases, the injection reestablishes a fluid viscosity close to that of water.

As oxidizing compound, mention may be made of bleach (aqueous solutions of a hypochlorite salt), hydrogen peroxide, ozone, chloramines, persulfates, permanganates or perchlorates.

The chemical nature of the surfactant compound(s) is not critical. They may be anionic, nonionic, amphoteric, zwitterionic and/or cationic. Preferably, the surfactant compound(s) of the invention bear anionic charges.

Preferably, the surfactant compounds used are chosen among anionic surfactants and their zwitterions chosen from the group comprising alkylsulfate, alkylethersulfate, arylalkylsulfate, arylalkylethersulfate, alkylsulfonate, alkylethersulfonate, arylalkylsulfonate, arylalkylethersulfonate, alkylphosphate, alkyletherphosphate, arylalkylphosphate, arylalkyletherphosphate, alkylphosphonate, alkyletherphosphonate, arylalkylphosphonate, arylalkyletherphosphonate, alkylcarboxylate, alkylethercarboxylate, arylalkylcarboxylate, arylalkylethercarboxylate, alkyl polyethers, arylalkyl polyether derivatives, etc.

Alkyl chain is defined as a 6 to 24 carbon atom chain, branched or not, with or without several units, that can optionally include one or more heteroatoms (O, N, S). Arylalkyl chain is defined as a 6 to 24 carbon atom chain, branched or not, that includes one or more aromatic rings and may optionally include one or more heteroatoms (0, N, S).

The most commonly used surfactants, for cost, stability and availability reasons, are of the sulfonate or sulfate type, presented in the form of alkali metal or ammonium salts.

A fourth feature of the invention relates to a friction reduction process for a fracturation fluid in a hydraulic fracturation operation for unconventional underground oil or gas reservoirs comprising the preparation of a fracturation fluid as described previously, and the injection of said fracturation fluid in an underground formation.

Friction reduction reduces or removes the losses related to friction during the injection of the fracturation fluid.

The invention and resulting benefits will become clear from the following exemplary embodiments.

EXAMPLES

Polymer Synthesis
Polymers 1 and 2 (Post-Hydrolyzed ATBS/Acrylamide Copolymers)
Polymer 1 (ATBS in Hydrated Crystalline Form)

To a 2000 mL beaker are added 761.9 g of deionized water, 574.2 g of 50% acrylamide solution, 35.9 g of 50% sodium hydroxide, 11.7 g of urea and 116.3 g crystals of 2-acrylamido-2-methylpropane sulfonic acid (hydrated crystalline form).

The resulting solution is cooled between 0 and 5° C. and transferred to an adiabatic polymerization reactor, then nitrogen is bubbled for 30 minutes to remove all traces of dissolved oxygen.

The following are then added to the reactor:
0.45 g of 2,2'-azobisisobutyronitrile,
1.5 mL of a 5 g/L solution of 2,2'-azobis[2-(2-imidazolin-2-yl)propane] dihydrochloride,
1.5 mL of a solution at 1 g/L of sodium hypophosphite,
2.25 mL of a solution at 1 g/L of tert-butyl hydroperoxide,
3.0 mL of a solution at 1 g/L of ammonium iron (II) sulfate hexahydrate (Mohr's salt).

After a few minutes, the nitrogen inlet is shut and the reactor is closed. The polymerization reaction occurs for 2 to 5 hours until a temperature peak is reached. The gel obtained is chopped into particles with a size inclusively between 1 and 6 mm.

500.0 g of previously chopped gel is then mixed with 18.0 g of 50% sodium hydroxide, the mixture is taken and held at a temperature of 90° C. for a duration of 90 minutes.

The gel is then dried and milled to obtain the polymer in powder form.
Polymer 2 (ATBS not in Hydrated Crystalline Form)

Polymer 2 is prepared like polymer 1, replacing the hydrated crystalline form of 2-acrylamido-2-methylpropane sulfonic acid with 2-acrylamido-2-methylpropane sulfonic acid that is not the hydrated crystalline form.
Polymers 3 and 4 (Acrylic Acid/a TBS/Acrylamide Terpolymers)
Polymer 3 (ATBS in Hydrated Crystalline Form)

To a 2000 mL beaker are added 542.1 g of deionized water, 558.7 g of 50% acrylamide solution, 104.8 g of 50% sodium hydroxide, 75.5 g of glacial acrylic acid, 15.3 g of urea and 203.6 g of crystals of 2-acrylamido-2-methylpropane sulfonic acid.

The resulting solution is cooled between 0 and 5° C. and transferred to an adiabatic polymerization reactor, then nitrogen is bubbled for 30 minutes to remove all traces of dissolved oxygen.

The following are then added to the reactor:
1.13 g of 2,2'-azobisisobutyronitrile,
1.5 mL of a 15 g/L solution of 2,2'-azobis[2-(2-imidazolin-2-yl)propane] dihydrochloride,
1.5 mL of a solution at 3 g/L of sodium hypophosphite,
0.75 mL of a solution at 1 g/L of tert-butyl hydroperoxide,
2.25 mL of a solution at 1 g/L of sodium persulfate,
1.5 mL of a solution at 2 g/L of ammonium iron (II) sulfate hexahydrate (Mohr's salt).

After a few minutes, the nitrogen inlet is shut and the reactor is closed. The polymerization reaction occurs for 1 to 5 hours until a temperature peak is reached. The gel obtained is chopped into particles with a size inclusively between 1 and 6 mm.

The gel is then dried and milled to obtain the polymer in powder form.
Polymer 4 (ATBS not in Hydrated Crystalline Form)

Polymer 4 is prepared like polymer 3, replacing the hydrated crystalline form of 2-acrylamido-2-methylpropane sulfonic acid with 2-acrylamido-2-methylpropane sulfonic acid that is not the hydrated crystalline form.
Polymers 5 and 6 (a TBS Homopolymers)
Polymer 5 (ATBS in Hydrated Crystalline Form)

To a 2000 mL beaker are added 390.5 g of deionized water, 262 g of 50% sodium hydroxide and 847.5 g crystals of 2-acrylamido-2-methylpropane sulfonic acid.

The resulting solution is cooled between 5 and 10° C. and transferred to an adiabatic polymerization reactor, then nitrogen is bubbled for 30 minutes to remove all traces of dissolved oxygen.

The following are then added to the reactor:
0.45 g of 2,2'-azobisisobutyronitrile,
1.5 mL of a solution at 2.5 g/L of 2,2'-azobis[2-(2-imidazolin-2-yl)propane] dihydrochloride,
1.5 mL of a solution at 1 g/L of sodium hypophosphite,
1.5 mL of a solution at 1 g/L of tert-butyl hydroperoxide,
1.5 mL of a solution at 1 g/L of ammonium iron (II) sulfate hexahydrate (Mohr's salt).

After a few minutes, the nitrogen inlet is shut and the reactor is closed. The polymerization reaction occurs for 2 to 5 hours until a temperature peak is reached. The gel obtained is chopped and dried to obtain a coarse powder itself milled and sieved to obtain the polymer in powder form.
Polymer 6 (ATBS not in Hydrated Crystalline Form)

Polymer 6 is prepared like polymer 5, replacing the hydrated crystalline form of 2-acrylamido-2-methylpropane sulfonic acid with 2-acrylamido-2-methylpropane sulfonic acid that is not the hydrated crystalline form.
Polymers 7 and 8 (a TBS/Acrylamide Copolymers)
Polymer 7 (ATBS not in Hydrated Crystalline Form)

To a 2000 mL beaker are added 549.5 g of deionized water, 520.5 g of 50% acrylamide solution, 97.6 g of 50% sodium hydroxide, 16.2 g of urea and 316.2 g crystals of 2-acrylamido-2-methylpropane sulfonic acid.

The resulting solution is cooled between 0 and 5° C. and transferred to an adiabatic polymerization reactor, then nitrogen is bubbled for 30 minutes to remove all traces of dissolved oxygen.

The following are then added to the reactor:
0.75 g of 2,2'-azobisisobutyronitrile,
1.5 mL of a 5 g/L solution of 2,2'-azobis[2-(2-imidazolin-2-yl)propane] dihydrochloride,
1.5 mL of a solution at 3 g/L of sodium hypophosphite,
2.25 mL of a solution at 1 g/L of tert-butyl hydroperoxide,
2.25 mL of a solution at 1 g/L of ammonium iron (II) sulfate hexahydrate (Mohr's salt).

After a few minutes, the nitrogen inlet is shut and the reactor is closed. The polymerization reaction occurs for 1 to 5 hours until a temperature peak is reached. The gel obtained is chopped into particles with a size inclusively between 1 and 6 mm The gel is then dried and milled to obtain the polymer in powder form.

Polymer 8 (ATBS not in Hydrated Crystalline Form)

Polymer 8 is prepared like polymer 7, replacing the hydrated crystalline form of 2-acrylamido-2-methylpropane sulfonic acid with 2-acrylamido-2-methylpropane sulfonic acid that is not the hydrated crystalline form.

Example 2: Preparation of Fracturation Fluids

Polymers 1 to 8 in powder form are dissolved with stirring at a concentration of 10,000 ppm in a brine composed of water, 85 g of sodium chloride (NaCl) and 33.1 g of calcium chloride ($CaCl_2$), $2H_2O$) per liter of brine.

The resulting saline polymer solutions are then injected into a 0.05 pptg concentration into brine recirculating for the Flow Loop tests that follow.

Example 3: Flow Loop Friction Reduction Tests

To evaluate the friction reduction for each of polymers 1 to 8, the reservoir in the flow loop was filled with 20 L of brine (brine described in example 2). The brine is then recirculated in the flow loop at a rate of 24 gallons per minute. The polymer is added at a concentration of 0.5 pptg in the recirculated brine. The friction reduction percentage is then determined using measurement of pressure variations measured inside the flow loop.

Figure 2:
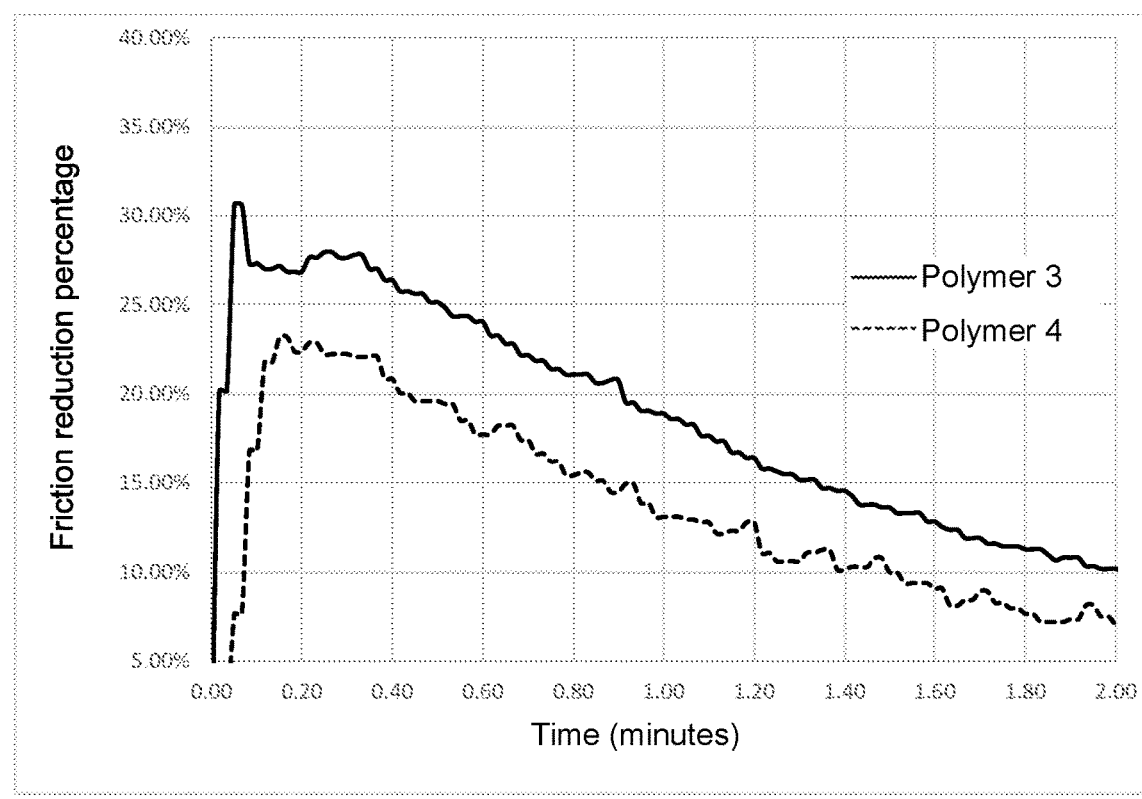
Figure 3:
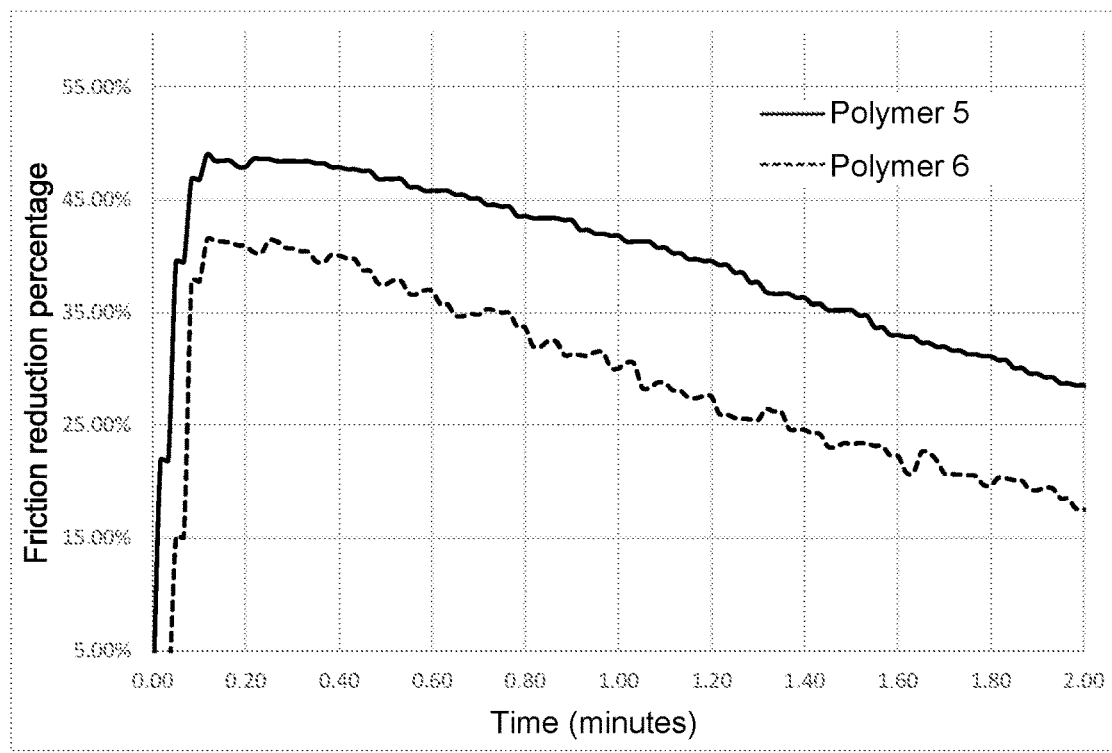
Figure 4:
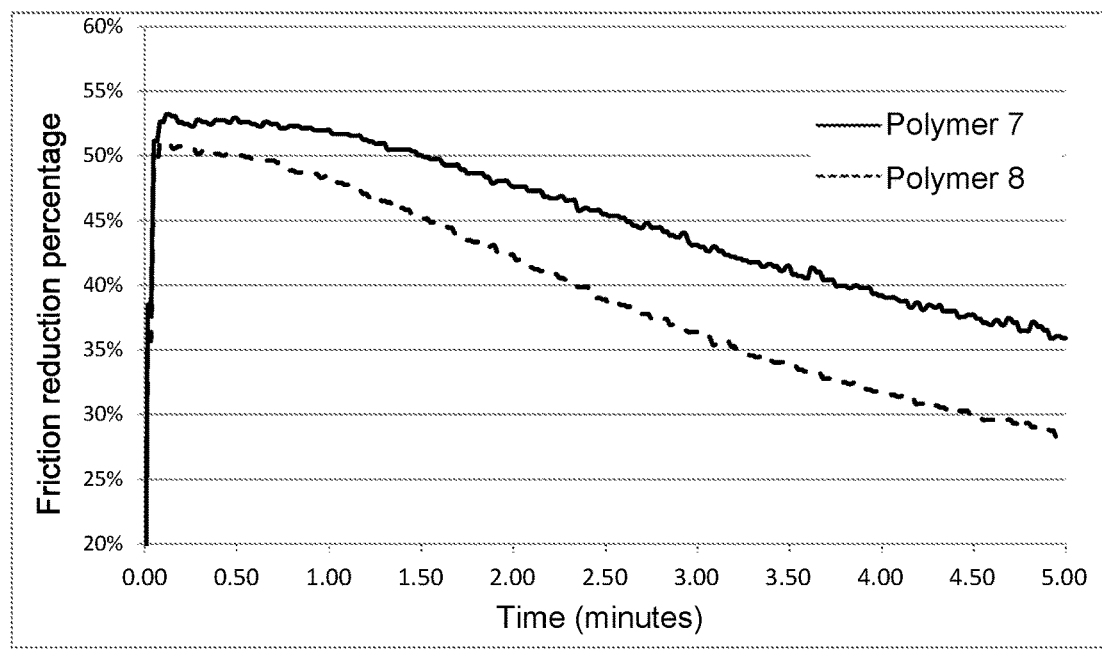

FIGS. 1 to 4:

FIGS. 1 to 4 are graphics showing the percentage of friction reduction as a function of time for each type of polymer. (FIG. 1: post hydrolyzed, FIG. 2: terpolymers, FIG. 3: copolymers, FIG. 4: homopolymers)

These figures show that the injection fluids according to the invention produce improved friction. Indeed, when the polymers contain ATBS in hydrated crystalline form, the friction reduction is better.

The invention claimed is:

1. A fracturing fluid comprising water, at least one propping agent and at least one water-soluble (co)polymer prepared from a hydrated crystalline form of 2-acrylamido-2-methylpropane sulfonic acid and/or of at least one of its salts;
   wherein the hydrated crystalline form of 2-acrylamido-2-methylpropane sulfonic acid has a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, and 46.04° degrees, all peak values being +/−0.1°.

2. The fracturing fluid according to claim 1, wherein the water-soluble (co)polymer is obtained at least from 2-acrylamido-2-methylpropane sulfonic acid and/or from at least one of its salts, 50 mol % to 100 mol % of 2-acrylamido-2-methylpropane sulfonic acid being in the hydrated crystalline form and/or at least from one of its salts.

3. The fracturing fluid according to claim 1, wherein the water-soluble (co)polymer is obtained from the hydrated crystalline form of 2-acrylamido-2-methylpropane sulfonic acid and/or from at least one of its salts, and from at least one nonionic monomer, and/or at least one anionic monomer, and/or at least one cationic monomer and/or at least one zwitterionic monomer.

4. The fracturing fluid according to claim 1, wherein the at least one water-soluble (co)polymer is prepared by polymerization of one or more monomers including the 2-acrylamido-2-methylpropane sulfonic acid in hydrated crystalline form, wherein said 2-acrylamido-2-methylpropane sulfonic acid in hydrated crystalline form is partially or totally salified before polymerization.

5. The fracturing fluid according to claim 1, wherein the water-soluble (co)polymer is anionic or amphoteric and comprises between 1 and 99 mol % of anionic monomers.

6. The fracturing fluid according to claim 1, wherein the water-soluble (co)polymer is a copolymer of a salt of the hydrated crystalline form of 2-acrylamido-2-methylpropane sulfonic acid and acrylamide.

7. The fracturing fluid according to claim 1, wherein the water-soluble (co)polymer is an anionic polymer obtained by copolymerization of a salt in the hydrated crystalline form of 2-acrylamido-2-methylpropane sulfonic acid with an acrylic acid salt, or an anionic polymer obtained by copolymerization of a salt of 2-acrylamido-2-methylpropane sulfonic acid in hydrated crystalline form with a nonionic hydrolyzable monomer.

8. The fracturing fluid according to claim 1, wherein the fracturing fluid comprises between 0.001% and 1% by weight of water-soluble (co)polymer prepared from the hydrated crystalline form of 2-acrylamido-2-methylpropane sulfonic acid and/or of at least one of its salts.

9. A preparation process for the fracturing fluid according to claim 1, the process comprising using, in water or brine, at least one water-soluble (co)polymer prepared from the hydrated crystalline form of 2-acrylamido-2-methylpropane sulfonic acid and/or of at least one of its salts, and in which the water-soluble (co)polymer is, before formation of the fracturing fluid:
   either in powder form;
   or in the form of a water-in-oil inverse emulsion;
   or in the form of an aqueous or oil particulate polyphasic suspension.

10. The process according to claim 9, wherein the water-soluble (co)polymer is, before formation of the fracturing fluid, in powder form having a particle size less than 1.5 millimeters.

11. The process according to claim 9, wherein the water-soluble (co)polymer is, before formation of the fracturing fluid, in the form of an inverse water-in-oil emulsion, the (co)polymer concentration in the emulsion being inclusively between 5 and 60% by weight relative to the weight of the emulsion.

12. The process according to claim 9, wherein the water-soluble (co)polymer is, before formation of the fracturing fluid, in the form of an inverse water-in-oil emulsion containing by weight from 0.01 to 70% of an organic and/or inorganic salt, relative to the weight of the emulsion.

13. The process according to claim 9, wherein the water-soluble (co)polymer is, before formation of the fracturing fluid, in the form of an aqueous particulate polyphasic suspension comprising:

- i 15 to 60% by weight of at least one water-soluble (co)polymer in the form of solid particles with average size inclusively between 5 and 500 μm;
- ii 15 to 45% by weight of at least one alkali metal salt and/or of at least one alkaline earth metal salt;
- iii at least one viscosifying agent other than the water-soluble (co)polymer;
- iv at least 10% by weight of water;

said suspension having a Brookfield viscosity inclusively between 500 and 20,000 cps at a temperature of 20° C., and said suspension having a density inclusively between 1.1 and 2 kg·L$^{-1}$.

14. The preparation process according to claim 9, wherein the water-soluble (co)polymer is, before formation of the fracturing fluid, in form of an oil particulate polyphasic suspension comprising:
- i 15 to 60% by weight of at least one water-soluble (co)polymer in the form of solid particles with average size inclusively between 5 and 500 μm;
- ii at least one viscosifying agent other than the water-soluble (co)polymer;
- iii at least 10% by weight of oil;

said suspension having a Brookfield viscosity inclusively between 500 and 20,000 cps at a temperature of 20° C., and said suspension having a density inclusively between 0.6 and 1.4 kg·L$^{-1}$.

15. A hydraulic fracturing process for an unconventional underground oil or gas reservoir comprising preparing the fracturing fluid according to claim 1, and injecting said fracturing fluid in an underground formation.

16. A friction reduction process for a fracturing fluid in a hydraulic fracturing operation for unconventional underground oil or gas reservoirs comprising preparing the fracturing fluid according to claim 1, and injecting said fracturing fluid in an underground formation.

17. The process according to claim 10, wherein the water-soluble (co)polymer is, before formation of the fracturing fluid, in powder form having a particle size less than 850 micrometers.

18. The process according to claim 17, wherein the water-soluble (co)polymer is, before formation of the fracturing fluid, in powder form having a particle size less than 200 micrometers.

19. The process according to claim 9, wherein the water-soluble (co)polymer is, before formation of the fracturing fluid, in the form of an inverse water-in-oil emulsion, the (co)polymer concentration in the emulsion being inclusively between 15 and 40% by weight relative to the weight of the emulsion.

20. The process according to claim 19, wherein the water-soluble (co)polymer is, before formation of the fracturing fluid, in the form of an inverse water-in-oil emulsion containing by weight from 0.01 to 70% of an organic and/or inorganic salt.

\* \* \* \* \*